(12) United States Patent
Prisco et al.

(10) Patent No.: US 11,992,679 B2
(45) Date of Patent: May 28, 2024

(54) SYSTEM AND METHOD FOR STIMULATION OF NERVE TISSUE

(71) Applicant: Medtronic Xomed, Inc., Jacksonville, FL (US)

(72) Inventors: John R. Prisco, Holly Springs, GA (US); David C. Hacker, Jacksonville, FL (US); Matthew L. Cantwell, Orange Park, FL (US); Anirudhan Narasimhan, Plymouth, WI (US); Amber A. Katada, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 431 days.

(21) Appl. No.: 17/178,848

(22) Filed: Feb. 18, 2021

(65) Prior Publication Data
US 2022/0257940 A1    Aug. 18, 2022

(51) Int. Cl.
| | | |
|---|---|---|
| *A61N 1/36* | (2006.01) | |
| *A61B 5/395* | (2021.01) | |
| *A61B 17/00* | (2006.01) | |
| *A61B 34/00* | (2016.01) | |
| *A61N 1/04* | (2006.01) | |

(52) U.S. Cl.
CPC ............ *A61N 1/3603* (2017.08); *A61B 5/395* (2021.01); *A61B 2017/00115* (2013.01); *A61B 34/76* (2016.02); *A61N 1/0456* (2013.01)

(58) Field of Classification Search
CPC ................ A61N 1/3603; A61N 1/0456; A61N 1/36017; A61B 34/76; A61B 5/389; A61B 5/395; A61B 5/4041; A61B 5/6848; A61B 2017/00115; A61B 2017/00039; A61B 18/1233
See application file for complete search history.

(56) References Cited

U.S. PATENT DOCUMENTS

| | | | |
|---|---|---|---|
| 10,039,915 B2 | 8/2018 | McFarlin et al. | |
| 10,105,140 B2 * | 10/2018 | Malinouskas | A61B 90/98 |
| 10,342,452 B2 | 7/2019 | Sterrantino et al. | |
| 10,349,862 B2 | 7/2019 | Sterrantino et al. | |
| 10,849,517 B2 | 12/2020 | Cantwell et al. | |
| 2006/0025702 A1 | 2/2006 | Sterrantino et al. | |
| 2008/0091089 A1 * | 4/2008 | Guillory | A61B 5/4094 600/301 |
| 2012/0123405 A1 * | 5/2012 | Moua | A61B 42/10 606/33 |
| 2014/0073985 A1 | 3/2014 | Sakai et al. | |
| 2014/0243677 A1 * | 8/2014 | Johnson | A61B 46/10 600/459 |

(Continued)

OTHER PUBLICATIONS

Extended European Search Report regarding Patent Application No. 22157599.6, dated Jul. 14, 2022.

*Primary Examiner* — Ankit D Tejani
*Assistant Examiner* — Joshua Brendon Solomon
(74) *Attorney, Agent, or Firm* — Carter, DeLuca & Farrell LLP

(57) ABSTRACT

A monitoring system may include a processor and display system for displaying results from the monitoring. A user may be in a sterile field away from the processor and display system and selected input devices. A controller may be physically connected to the monitoring system from the sterile field to allow the user to control the monitoring system.

20 Claims, 16 Drawing Sheets

(56) References Cited

U.S. PATENT DOCUMENTS

2015/0066026 A1* 3/2015 Hart .................. A61B 34/76
606/46
2016/0287112 A1 10/2016 Mcfarlin et al.
2018/0078161 A1 3/2018 Cantwell et al.
2018/0368849 A1* 12/2018 Swensgard ...... A61B 17/07207

* cited by examiner

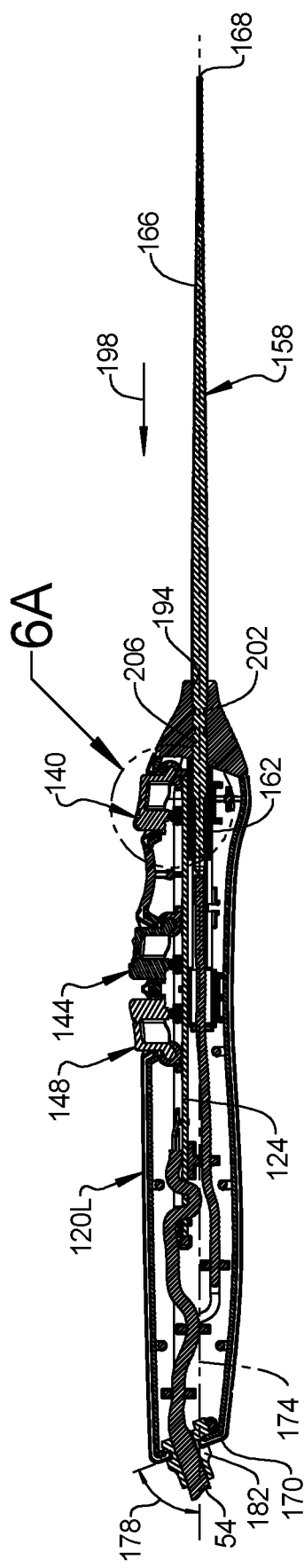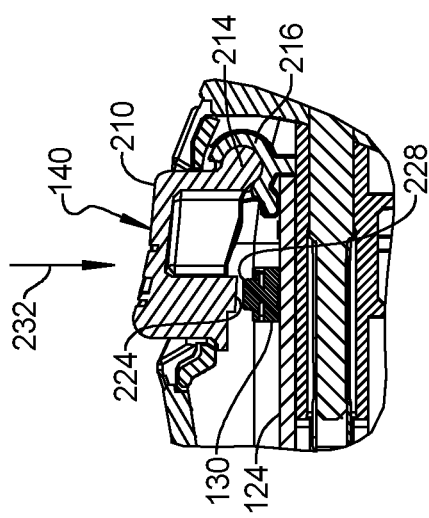
FIG. 6
FIG. 6A

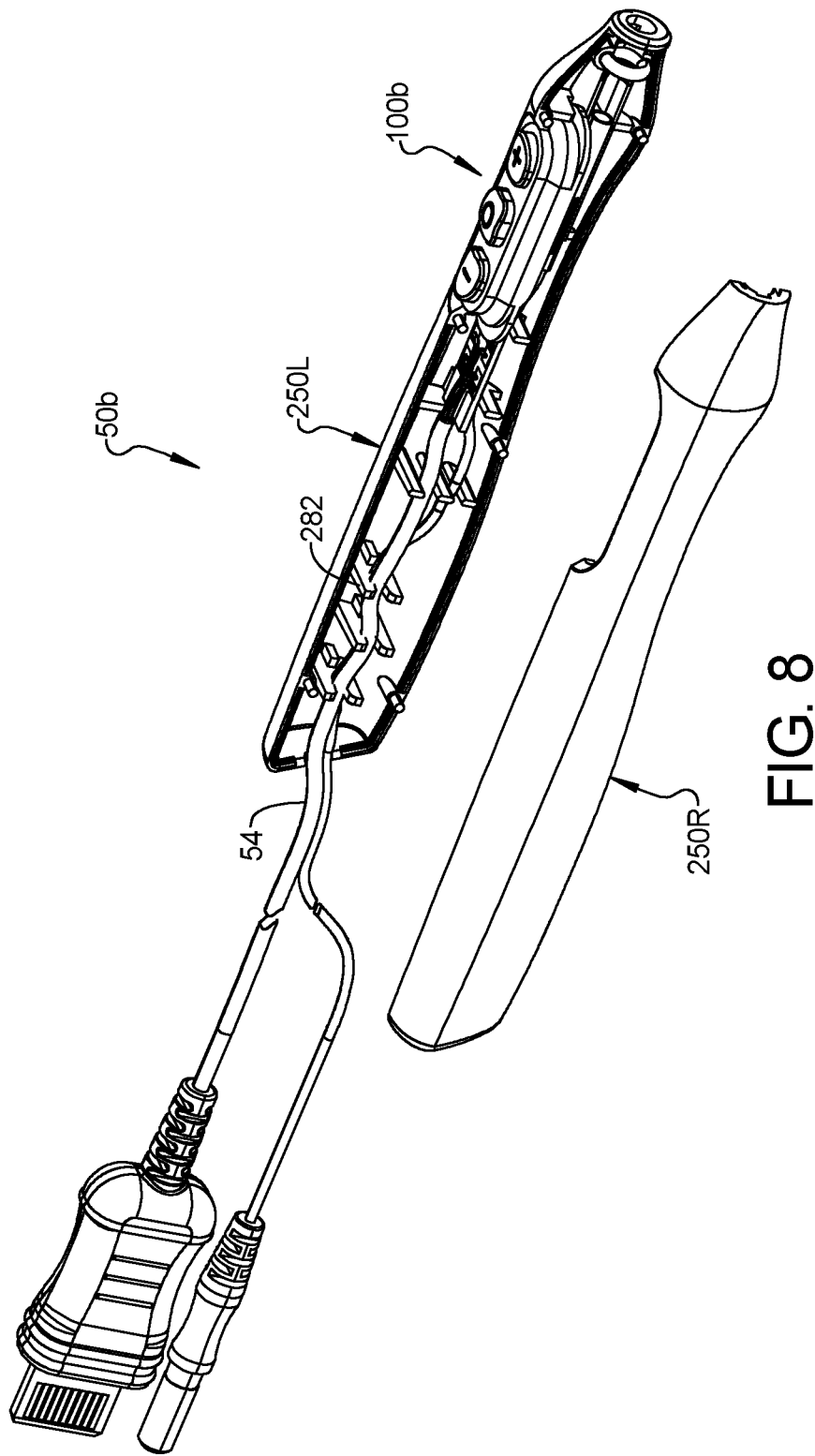

SYSTEM AND METHOD FOR STIMULATION OF NERVE TISSUE

FIELD

The present disclosure relates to nerve stimulation and nerve stimulators.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

A nerve of a patient may be stimulated by applying electrical energy to the nerve via a stimulation probe. The stimulation probe may include a stimulating electrode tip. A surgeon may touch a location on a patient with the electrode tip to provide a voltage and/or current to a location on the patient and stimulate nerve activity and may result in a muscle response (or muscle activity). A return (or anodal) needle may be attached: via a wire, to the mono-polar stimulation probe; and to the patient away from (i) sensors, and (ii) an area being stimulated. The sensors can include electrodes that are attached to the patient and used to monitor the muscle activity.

Nerve monitoring systems such as the NIM-Response® 3.0 and/or NIM-Neuro® 3.0 nerve monitoring systems, sold by Medtronic, Inc., may be used to monitor electromyography (EMG) responses. In particular, the monitoring systems may provide stimulation at a selected nerve and a response sensed or detected at muscles remote from the location of the stimulation. Monitoring the EMG responses may be used to determine whether one or more nerves has been damaged during a select procedure. In various systems, the monitoring system may be controlled by a monitor user that is spaced apart from a procedure user and a subject. Therefore, the monitor user may require instructions from the procedure user to operate the monitoring system according to a selected use by the procedure user.

SUMMARY

A stimulation probe is provided and includes at least a first electrode. The stimulation probe may further include a second electrode, particularly if a bipolar stimulation probe is selected. The stimulation probe system may further includes at least one of a control module and/or switches. The control module may be separate from the probe, but in communication therewith. In various embodiments, the switches may transmit a signal to the control module to increase a stimulation signal, decrease a stimulation signal, record a signal at a selected time, and/or provide control signals to the stimulation system.

A nerve monitoring system may be used to monitor the integrity of a nerve. During a procedure, a procedure user may operate and/or alter an operation of the nerve monitoring system with the switches provided for use by the procedure user. The switches may include hardware that can be manipulated by the procedure user at the procedure user's location. Therefore, instructions or control to the nerve monitoring system may be provided at a location remote from the monitoring system.

The monitoring system may include a processor and display system for displaying results from the nerve monitoring. The monitoring system, however, may not be immediately available for placement in a sterile field or for placement proximal to a subject. The subject may be monitored with the monitoring system for a selected procedure. The procedure user may include a surgeon. The surgeon may be sterile for the selected procedure. Switches may be connected to a monitoring and/or stimulating instrument during a procedure. Switches may also or alternatively be connected adjacent to or to the surgeon and connected with the instrument and the monitoring system. The switches may be sterile and appropriate for placement in the sterile field.

The switches may include a physical connection to the monitoring system with a length of conductive material. The physical connection may include a wire (e.g. copper or aluminum wire), conductive polymer, or other appropriate conductive material. The physical connection may allow for both a signal from the remote to the monitoring system to interact with the monitoring system and/or to transmit a signal to and/or from the instrument.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The drawings described herein are for illustrative purposes only of selected embodiments and not all possible implementations, and are not intended to limit the scope of the present disclosure.

FIG. 2A is a side elevation view of the handle of the instrument as illustrated in FIG. 2;

FIG. 2B is a bottom elevation view of a handle of the instrument as illustrated in FIG. 2;

FIG. 6 is a cross-sectional view of the instrument taken along line 6-6 of FIG. 1;

FIG. 6A is a detailed cross-sectional view taken in circle 6a of FIG. 6;

FIG. 8 is a partial exploded view of the instrument of FIG. 7;

Corresponding reference numerals indicate corresponding parts throughout the several views of the drawings.

DETAILED DESCRIPTION

Example embodiments will now be described more fully with reference to the accompanying drawings.

Figure 1:
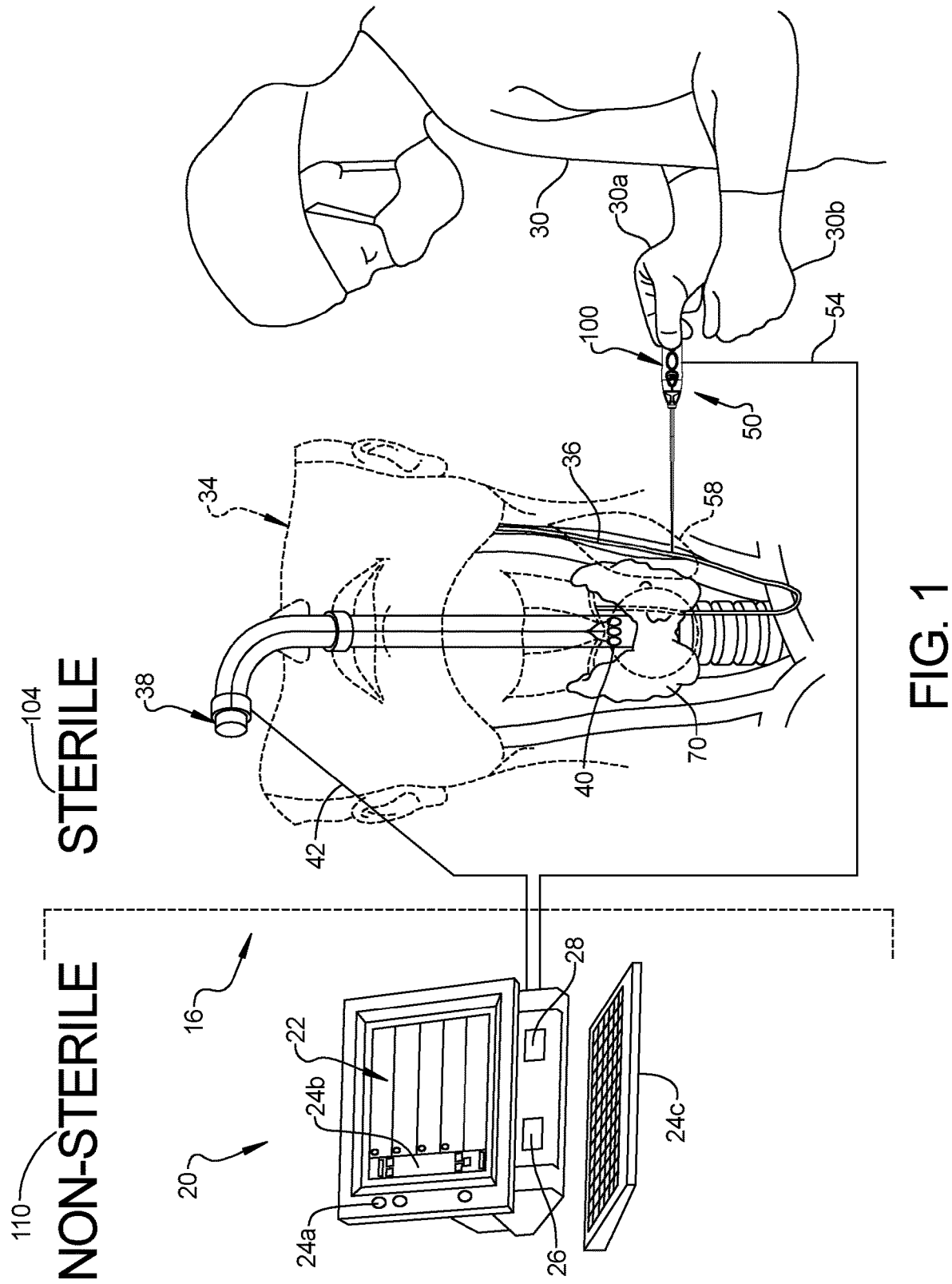
FIG. 1 is a schematic environmental view of a stimulation instrument used during a procedure.

With initial reference to FIG. 1 a monitoring system 16, such as a NIMø nerve integrity monitoring system, sold by Medtronic, Inc. having a place of business in Minneapolis, Minn., is illustrated in an environmental setting. The monitoring system may also include portions similar to those described in U.S. Pat. No. 10,849,517, issued Dec. 1, 2020, incorporated herein by reference. The monitoring system 16 may include a monitor assembly 20 that has a display screen or device 22 and one or more input devices. The input device may include one or more systems or structures to input commands of information such as a knob 24a, a touch screen 24b, a keyboard 24c, or other appropriate input devices. Input devices may also include other tactile input devices, audio input devices, visual input devices, etc.

The monitor assembly 20 may further include a processor 26 and a memory 28. It is understood that the processor 26 may access the memory 28 to execute instructions stored thereon or access other data stored with the memory 28. The memory 28 may include a physical memory, such as a spinning hard disk drive, solid state memory, or other appropriate types of memory. Further, the memory 28 may not be incorporated into the monitor assembly 20, but may be accessed by processor 26, such as via a communications network. The processor 26 may be a general purpose processor that is operable to execute instructions for generating a selected output, as discussed further herein. The processor 26 may further include onboard memory. Moreover, the processor 26 may include a specific purpose processor such as an application specific integrated circuit (ASIC). Accordingly, the processor 26 may execute instructions stored on memory 28, which may be a non-transitory memory, to provide an output for display on the display device 22.

The monitoring system 20 may further include a stimulation portion and/or generator. The stimulation portion may be configured to generate a voltage based upon control by the processor 26. The processor 26 may execute instructions of a program stored on the memory 28 and/or control by a user 30. As discussed herein, the monitoring system 20, therefore, may be operated to generate a stimulation at or with a stimulation instrument based upon control of the user 30.

The information displayed on the display device 22 may include information selected by the user 30. The selection made by the user 30 may be desired or selected information regarding a subject 34. The subject 34 is illustrated as a human subject, but it is understood that the subject may be any appropriate living subject, including non-human subjects. Further, the monitoring system 16 may be used with non-living subjects. Non-living subjects may have systems that are selected to be monitored for selected activity, such as electrical activity, and the monitoring system 16 may be used. In selected embodiments, however, the user 30 may be performing a surgical procedure on the subject 34. The user 30, therefore, may select to monitor nerve response and/or integrity such as by monitoring electromyography (EMG) responses.

One or more stimulation or monitoring assemblies may be incorporated in the monitoring system 16 and connected with the monitor assembly 20. For example, in various procedures such as a thyroidectomy or other thyroid surgeries, monitoring of a recurrent laryngeal nerve (RLN), a vagus nerve, or other appropriate nerve 36, in the subject 30. Other or alternative nerves may also be monitored, including other selected cranial nerves and/or spinal nerves. Monitoring of the RLN may include a nerve monitoring esophageal tube 38, which may have one or more conductive electrodes 40 that are in contact with selected portions of the subject 34. The electrode 40 may be affixed to an exterior of the tube 38 and/or incorporated into the structure of the tube 38. The electrode 40 can be connected to the monitor assembly 20 via a connection 42.

In addition, other instruments may be connected to the monitor assembly 20, such as electrode assemblies, including an electrode that may send or receive periodic stimulation pulses. In various embodiments, one or more stimulation instruments 50 may be used. The stimulation instrument 50 may be connected to the monitor assembly 20 with a connector 54. The connector 54 may allow for a physical connection between the stimulation instrument 50 and the monitoring assembly 20. The connector 54 may include a conductive member (e.g. a metal wire, conductive polymer, etc.). The stimulation instrument 50 may include various instruments such as surgical instruments and the like. Examples of various types of stimulation instruments include those disclosed in U.S. Pat. No. 10,039,915 issued on Aug. 7, 2018 and U.S. Pat. App. Pub. No. 2016/0287112 published on filed Oct. 6, 2016; both incorporated herein by reference.

According to various embodiments, for example as illustrated in FIGS. 2, 2A, 2B, 3, 4, 5, and 6 the instrument 50 is illustrated as an instrument 50a that may include the switches 100 as switches 100a. It is understood that in various embodiments the instrument 50 may be provided to include features either separately and/or in combination as discussed further herein. Accordingly, discussion of the instrument 50a is understood to include various features that may be provided in the instrument 50a alone and/or in combination with other features as discussed further herein.

In various embodiments, therefore, the instrument 50a may include the switch or switch assembly 100a. The instrument 50a may include a housing or handle 120. In various embodiments, the housing 120 may include two portions which may include a first or left portion 120L and a second or right portion 120R. The two housing portions 120L, 120R may be formed separately, such as with a selected molding procedure, such as injection molding. The two housing portions 120L, 120R may then be fit and connected together to form the housing 120 of the instrument 50a. In various embodiments, the two housing portions 120L, 120R may be snap fit together, adhered together, mechanically connected, or otherwise assembled together into the housing 120. For example, the two housing portions 120L, 120R may be connected with an adhesive and/or sonically welded together.

Figure 2:
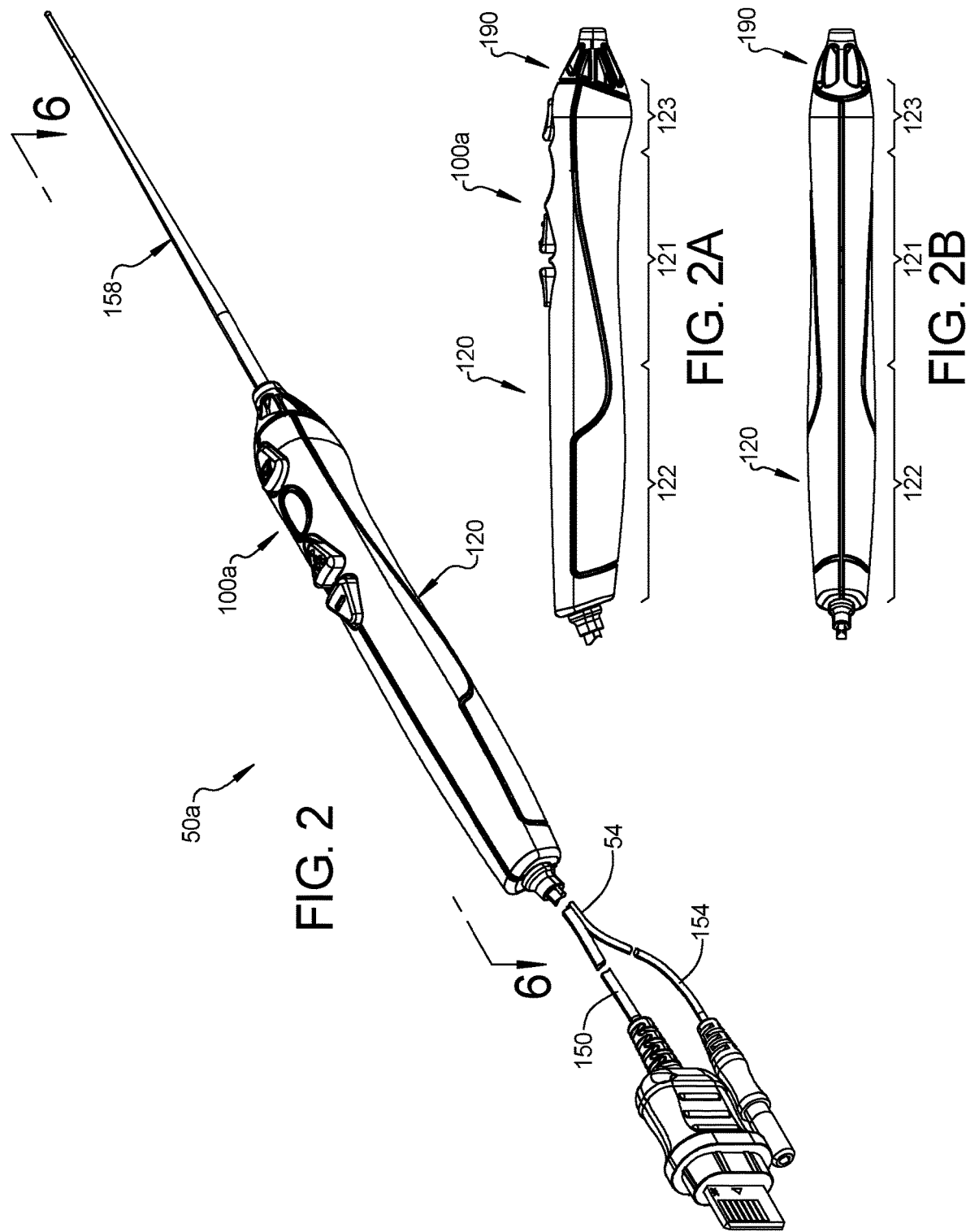
FIG. 2 is a perspective view of an instrument handle and connection cable, according to various embodiments.
Figure 3:
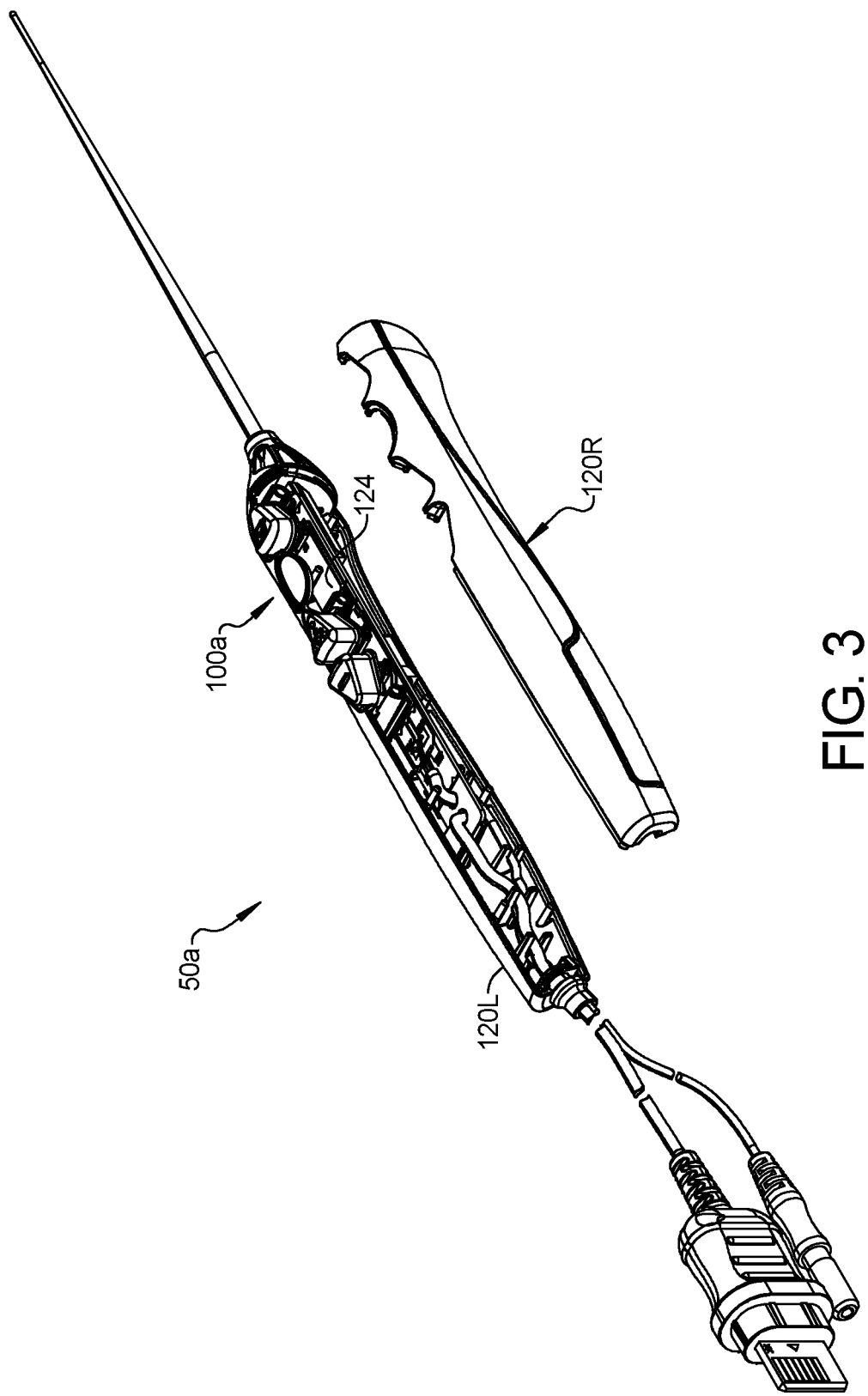
FIG. 3 is an exploded view of the instrument of FIG. 2.
Figure 4:
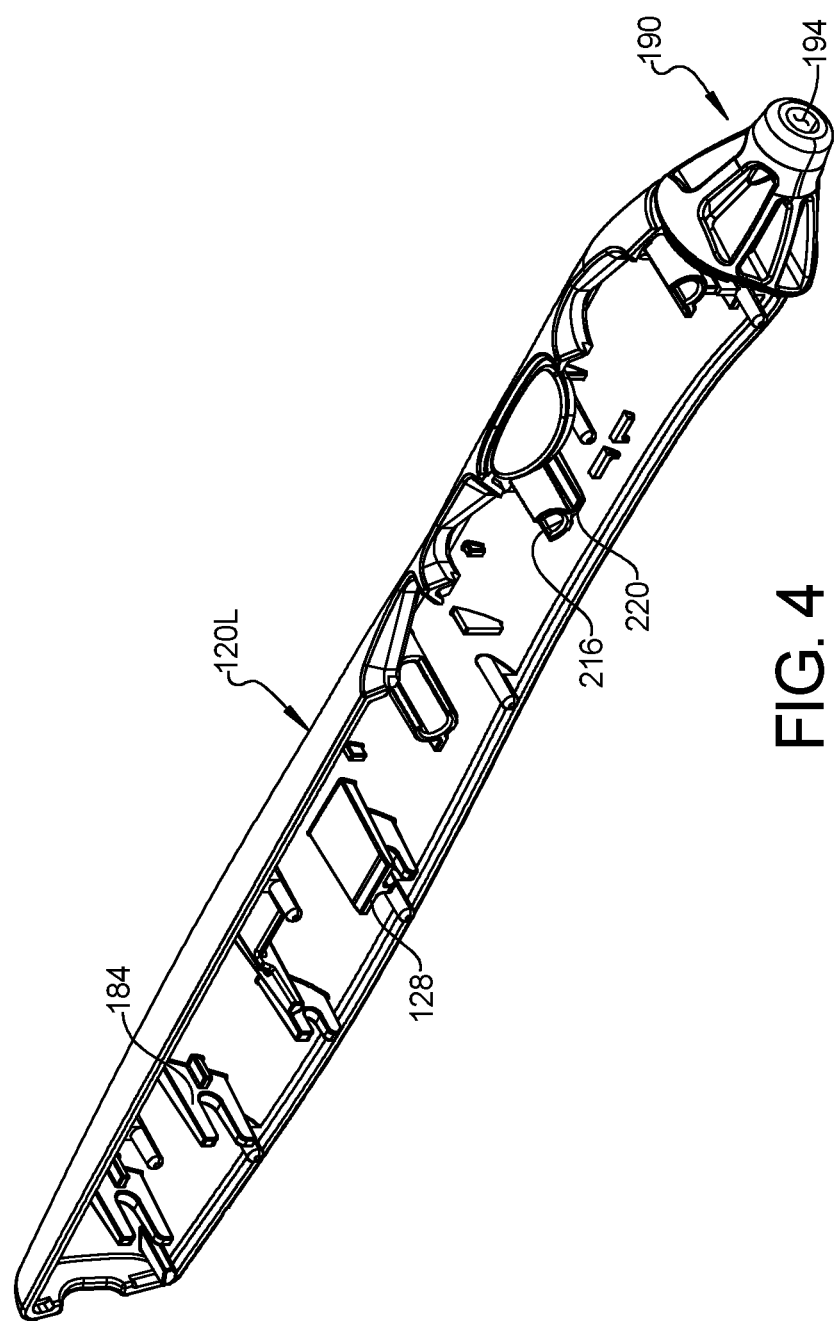
FIG. 4 is a detailed view of an interior portion of the housing of FIG. 2.
Figure 5:
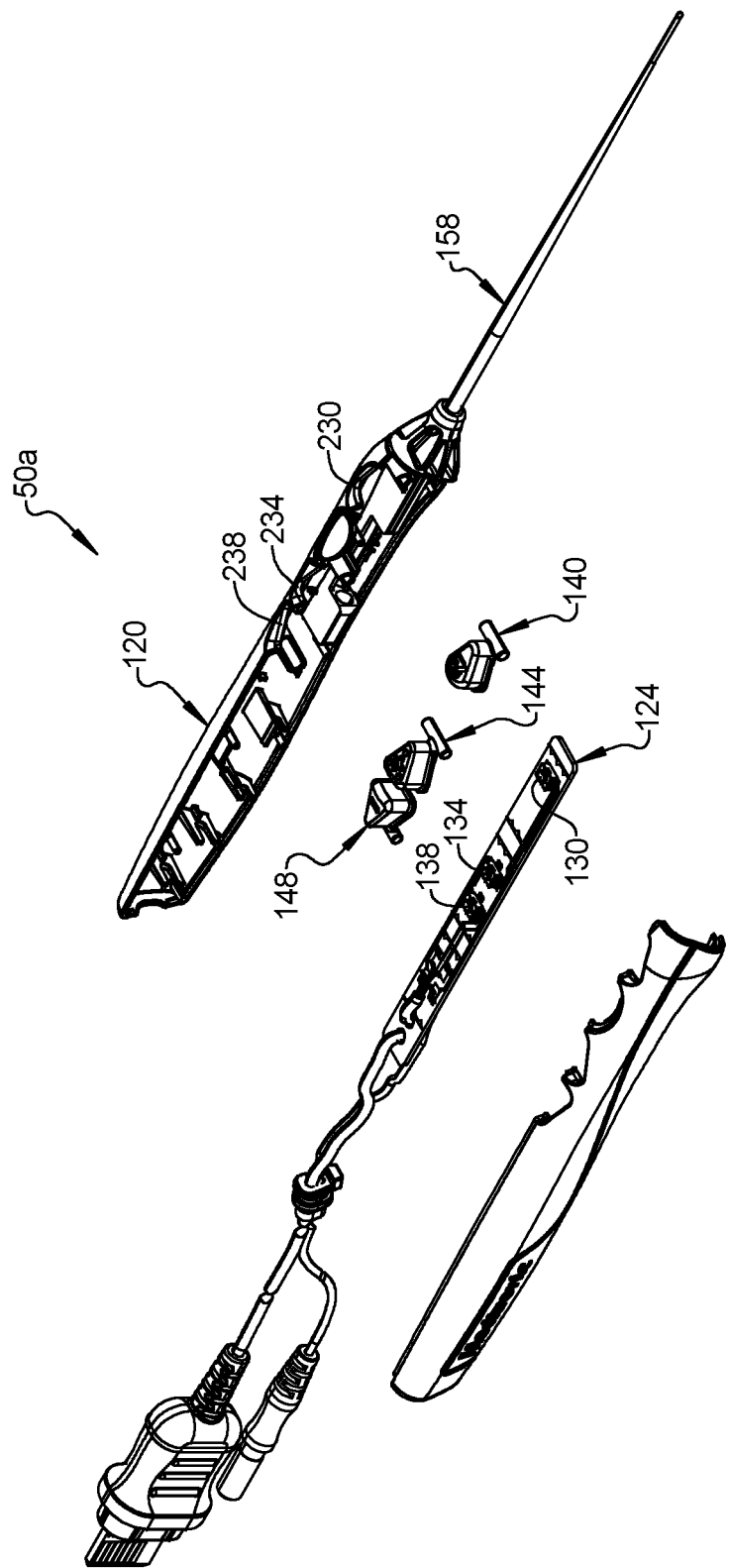
FIG. 5 is an exploded view of the instrument of FIG. 2.

The housing assembly 120 may include a selected geometry, as illustrated in FIGS. 2, 2A, and 2B. The geometry of the housing 120 may be provided to indicate to the user 30 by feel or touch an orientation and/or feature of the instrument 50a. The housing 120, therefore, may include a waist or center region 121 generally near the switch assembly 100a. The waist region 121 may include a minimum outer dimension, such as a circumference. The housing 120 may further include a swelled or enlarged portion region 122 proximal thereto relative to a distal end 190. The housing 120 may further include a proximal region 123 that may also be of an enlarged geometry relative to the waist region 121. Generally, the waist region 121 may have a selected external perimeter dimension that is smaller than either the enlarged region 123 and/or the proximal region 122. In various embodiments, the enlarged region 123 may have a maximum external perimeter to that of the proximal region 122.

In various embodiments, the housing 120 may house various portions such as a printed circuit board (PCB) 124 that is held in a selected location relative to the housing 120, such as the left housing 120L with one or more projections or stabilization portion, such as a projection 128. The PCB 124 may include or provide connections between various components, such as electrical switches including a first switch 130, a second switch 134, and a third switch 138. The switches 130-134 may be activated with pushbuttons or lever portions such as a first button portion 140, a second button portion 144, and a third button portion 148. Each of the switches 130-134 may be operated with one of the push buttons 140-144, thus allowing individual signaling with each switch. In various embodiments, more or less than three switches and/or push buttons may be provided.

The switches 130'138 may provide signals to the monitoring system 20 through various connectors, such the connector 54. The switches 130-134 may be appropriate switches, such as a KMR633NGLFG switch sold by C&K switches having a place of business in Waltham, Mass. The switches may require a selected force to activate to provide to a user a feedback regarding activation operation, such as about 1 Newton (N) to about 10 N, including about 1 N to about 5 N, including about 3 N. The switches may provide a signal through a control signal carrier lead or wire 150 that may include a plurality of pins or connections connecting to the controller 20. Further, a stimulation signal may be carried on a separate wire 154 that is connected directly to a probe or stimulation portion or member 158, also referred to as a probe or stimulation probe.

The switch assembly may provide a feedback to the user 30 regarding operation of depression of one or more of the switches 130-138. For example, the switch may provide an audible or tactile click, vibrate, illuminate, etc. Further, separate light emissions portions (e.g., light emitting diodes (LEDs)), vibration motors, speakers, etc. may provide auditory, tactile/haptic, and/or optical feedback to the user 30 regarding depression of one or more of the switches. The feedback may differ, such as a different sound and/or color of light, for each of the switches 130-138.

The stimulation member 158 may be connected to the stimulation lead 154 substantially directly with selected connection portion, such as a crimp socket or member 162. The crimp socket 162 may connect directly to the lead portion 158 such that a stimulation signal is provided directly from the controller 20 through the probe 158. In various embodiments the probe 158 may include an insulated cover 166 so that only a selected portion, such as a distal tip 168, is exposed. By having only the distal tip 168 exposed, the stimulation signal or voltage is provided only at the distal tip 168 and not along the length of the probe 158 due to the covering 166.

The housing 120 may be formed of the two portions or members 120L and 120R and fit together, as discussed above. Each of the housing portions 120L, 120R may have a selected geometry, such as a proximal end or region 170 that may extend at a non-perpendicular angle relative to a long axis 174 of the housing 120. The probe 158 may generally extend along the axis 174 and/or provided substantially parallel thereto. The rear wall 170 may extend at the angle 178 relative to the axis 174 for various purposes.

The angle 178 is generally about 50 degrees to about 85 degrees, including about 70 degrees. Further, a stress relief member or portion 182 may hold the wire or connector 54 relative to the housing 120 to assist in reducing strain and/or protecting the cable 54 from the or engagement with the housing 120. Further the housing portion, such as the housing 120L may include selected projections, such as projections 184 to engage or guide the cable 54 through the housing 120.

The housing 120, such as the left portion 120L, may include a distal end or region 190. The distal region 190 may be a substantially unitary member or portion that is formed as one piece. The distal end 190 may include a bore or passage 194. In various embodiments, the probe 158 may be press fit into the bore 194 by moving the probe 158 generally in the direction of arrow 198. The press fitting of the probe 158 into the bore 194 may allow for a frictional engagement of the probe 158 relative to the distal portion 190 of the housing 120. The probe 158 may include interference portions, such as depressions and/or ridges 202 to engage the distal portion 190.

In various embodiments, however, the housing portion 120L may be molded around the or about the probe 158. The probe 158 may include the interference portions 202 (e.g. splines, ridges, projections, etc.). The housing member 120L may be molded about or around the probe 158 such that the distal portion 190 captures or is molded around a proximal or end 206 of the probe 158. In various embodiments, for example, the distal portion 190 alone or with the housing portion 120L may be injection molded (i.e., overmolded) onto the probe 158. Thus, the probe 158 may be substantially held relative to the housing member 120L during a use. The connector 162 may be connected to the probe end 206, for example, after the housing member 120L is molded around the probe 158.

The PCB 124 may also be fit to the housing member 120L. The right housing member 120R may be connected to the first housing 120L. As discussed above, the PCB 124 may include a selected number of switches, such as the switches 130'138. Each of these switches 130'138 may be actuated by the respective push button members 140'148. In various embodiments, the connections of the switches 130-138 may be sealed to the PCB 124, such as with a flowable sealer, including the DOWSILú DOW3140 RTV coating, sold by DOW, having a place of business in Michigan.

With continuing reference to FIGS. 2'6, and with particular reference to FIG. 6 and FIG. 6A, each of the respective pushbuttons 140-148 may be activated or moved to encounter one or more of the respective switches 130-138. With reference to the push button 140, operation of the buttons and switches will be discussed. It is understood that each of the buttons and switches may be operated in a substantially similar manner, thus discussion of only the pushbutton 140 and the switch 130 is understood to relate to all of the pushbutton and switches.

The push button 140 may include a contact portion or surface 210. The surface 210 may be contacted by one or more digits of the user 30 to operate the selected switch. The button 140 may also include a rocker portion or projection 214 that may be received in a depression or groove 216 formed as or with a projection 220 within the housing, such the housing 120L. The projection 214 held within the groove 216 allows the button member 140 to move a selected distance, such as to operate or depress the switch 130. The switch 130 may be held by the PCB 124 such that the switch 130 does not substantially move relative to the housing 120L. By pushing on the surface 210, however, the button member 140 may move toward the switch 130 to activate or send a signal via the switch 130.

In various embodiments, the button member 140 may include a mass or projection or surface 224 that engages a push or activation surface or portion 228 of the switch 130. The button member 140, such as by pushing on the surface 210, generally in the direction of arrow 232 may allow the button member 140 to activate the respective switch 130. It is understood that each of the switches 130'138 may be operated in a substantially similar manner relative to and/or with the respective button members 144, 148.

Each of the respective switches may perform various features or functions. In various embodiments, the switch 130 may be operated by the button member 140 to provide a recording or notification at a selected time. As discussed above, the monitoring system 30 may be used to provide a signal for stimulation of a selected nerve and/or a location of a response relative to the nerve. The recording button 140 may provide a signal to the system 30 to record the signal at a selected time.

The other buttons may be used to increase or decrease a simulation. For example, the button member 144 may be operated to depress the switch 134 to increase a stimulation. The button 148 may be operated to operate the switch 138 to decrease stimulation. The increase and decrease buttons may be used to stepwise increase or decrease the stimulation a selected amount (e.g. steps of about 0.01 volts to about 0.1 volts per press).

The housing assembly 120 may include a bore or passage to allow movement of the button members 140 and access to the button members 140'148 by the user 30. For example, a first passage 230 may be formed through the housing member 120, a second passage 234, and a third passage 238 may allow for the respective buttons 140, 144, 148 to be accessed by the user 30. Thus, it is understood that the user 30 may operate the system 20 by using selected buttons in a selected manner. Further, the user 30 may move the probe tip 168 relative to the subject 34 by movement of the housing 120 that is engaged to the probe tip 158.

Figure 7:
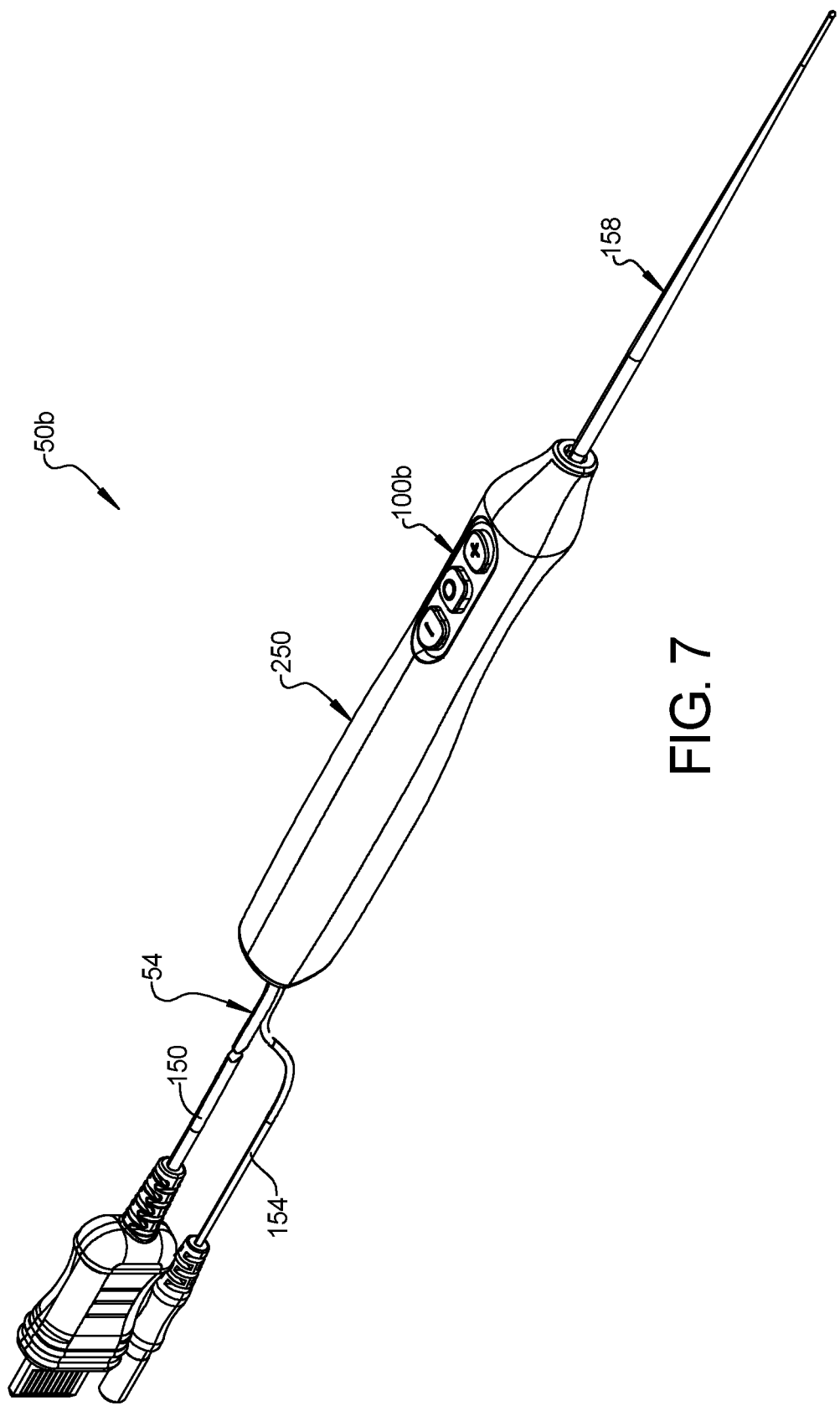
FIG. 7 is a perspective view of an instrument handle and connection cable, according to various embodiments.
Figure 7A:
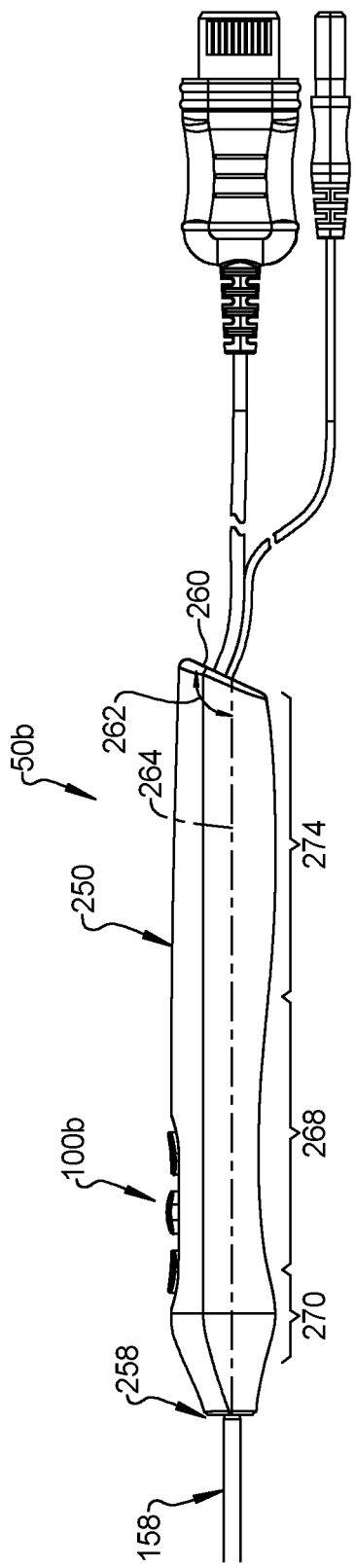
FIG. 7A is a side elevation view of the instrument of FIG. 7.
Figure 7B:
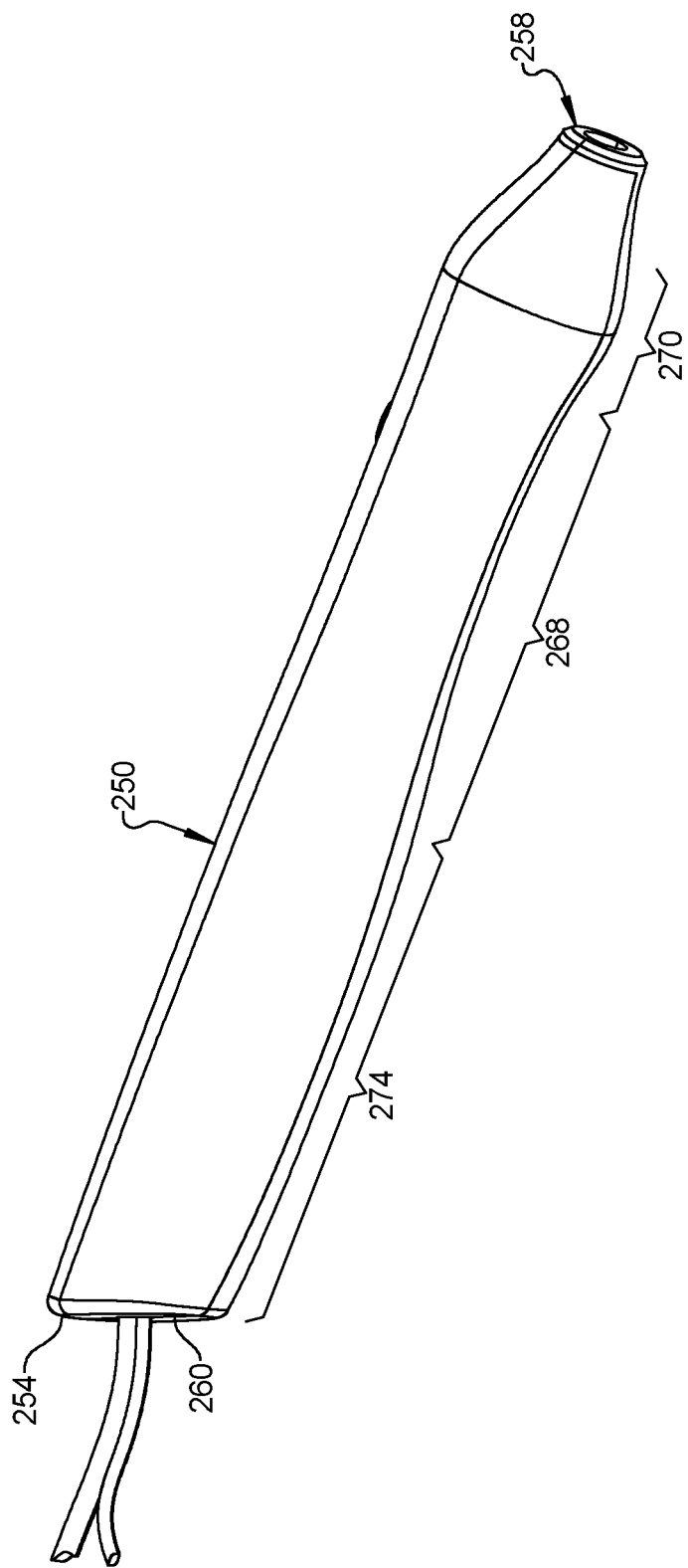
FIG. 7B is a side perspective detailed view of the instrument of FIG. 7.
Figure 9:
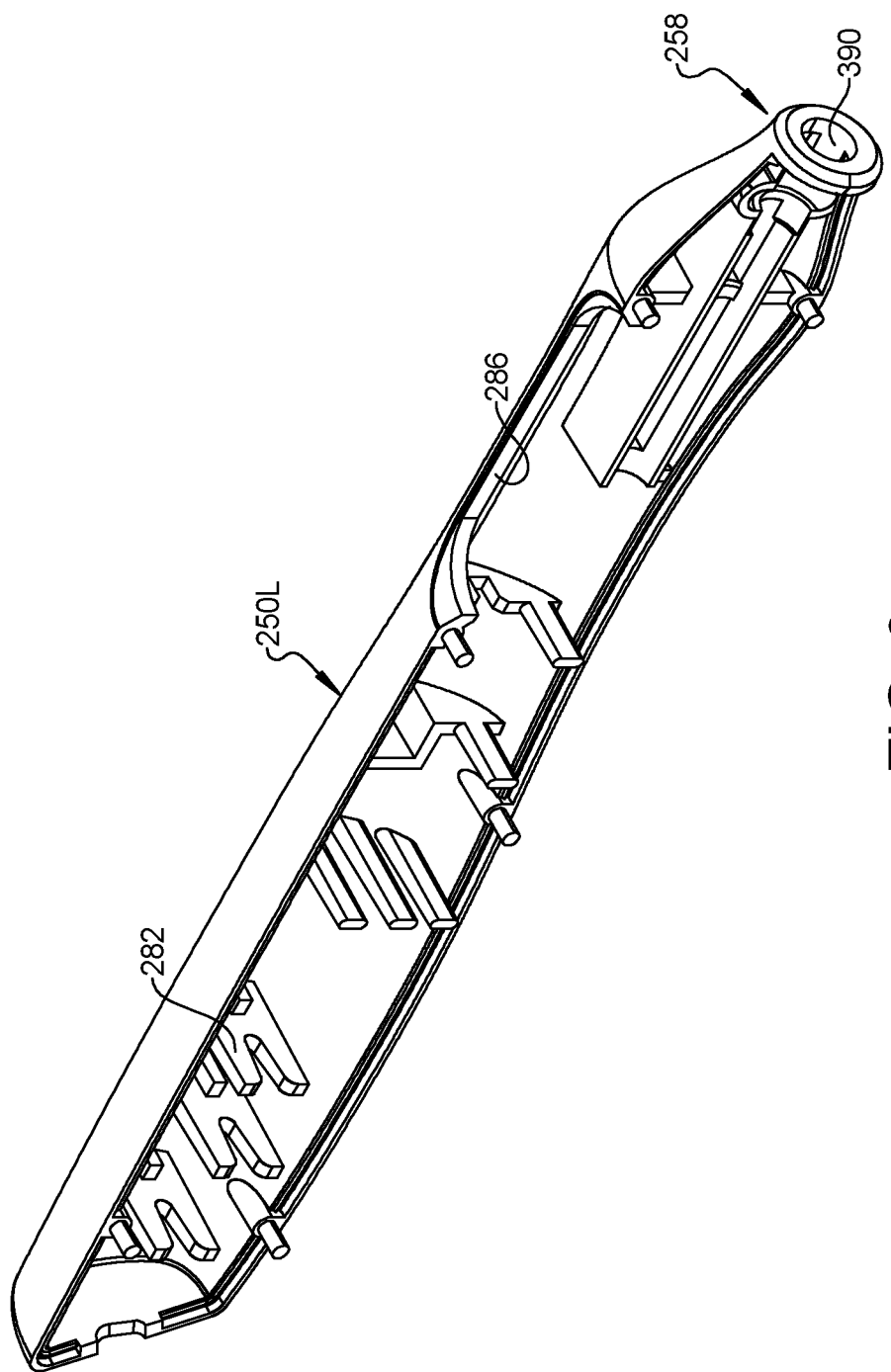
FIG. 9 is a detailed interior view of a housing portion of a housing of FIG. 7.

As discussed above, the instrument 50 may be provided in various embodiments including portions or elements that are discussed herein and may be included either alone and/or in combination with other elements. Accordingly, an instrument 50b and FIG. 7 is illustrated to include various features and portions. The instrument 50b may include a switch assembly portion 100b. The instrument assembly 50b may include various portions, such as those as discussed above and further herein, which may be included with various other embodiments and/or substituted herein or therein. Nevertheless, the instrument 50b will be described and illustrated in FIGS. 7, 7a, 7b, 8, 9, 10, and 11.

The instrument 50b may include the connector 54 similar to the connector 54 discussed above. The connector 54 may include two portions, such as the signal portion 150 and the stimulation portion 154. The two portions 150, 154 may be connected similarly as that discussed above, including the signal or control portion 150 transmitting signals from the switch assembly 100b and the stimulation connector 154 providing a stimulation signal or voltage to poll 158. Further, the probe 158 may be substantially similar or identical to the probe 158 as discussed above and will be discussed in detail here. It is understood, however, that to the stimulation signal may be transmitted through the stimulation connector 154 to the probe 158.

The instrument 50b may include a housing 250 that may be similar to the housing 120 discussed above. The housing 250 may include two portions such as a first or left portion 250L and a second or right portion 250R. The two portions 250L, 250R may be formed separately and assembled into a single housing assembly that may be grasped by the user 30. The two housing portions 250L, 250R may be interconnected and/or fixed together in an appropriate manner, such as that discussed above.

Further the housing portion 250 may extend from a proximal end 254 to a distal end 258. The housing 250 may include a rear or proximal wall 260 that may extend along a plane or axis that is at a non-perpendicular angle 262 to a long axis 264 of the housing 250. The non-perpendicular angle 262 may be defined relative to the long axis 264. The angle 262 is generally about 50 degrees to about 85 degrees, including about 70 degrees. The probe 158 may generally extend aligned with and/or parallel to the long axis 264.

The housing assembly 250, similar to that discussed above, further includes a waist or center region 268 generally near the switch assembly 100b and a swell or enlarged portion region 270 distal thereto relative to the proximal end 254. A proximal region 274 of the housing 250 may further include an enlarged geometry relative to the waist region 268. Generally, the waist region 268 may have a selected external perimeter dimension that is smaller than either the enlarged region 270 and/or the proximal region 274. Further, the enlarged region 270 may have a maximum external dimension or perimeter (e.g., circumference) of the housing 250. It is understood that the handle assembly 250 may include a similar geometry, as discussed or illustrated above.

The instrument 50b includes the switch assembly 100b, according to various embodiments. The switch assembly 100b may be positioned within the housing 250. The cable or connector 54 may be positioned within the housing 250. The cable 54 may be positioned or held within projections and strain releases 282 to assist in holding the connector 54 within the housing 250 during use and manipulation of the instrument 50b.

The switch assembly 100b may be positioned such that it may be accessed through an opening 286 formed within the housing 250. The switch assembly 100b may include depressible members 290, 294, and 298. All of the depressible members 290' 298 may be formed as a single unitary member or button portion 300. It is understood, however, any appropriate number of depressible portions may be provided greater or less than three as well. The button portion 300 may be formed of a selected material, such as silicone rubber or equivalent material. The button portion 300 may be covered by a button cover 304 that has one or more passages 306 to allow access to the individual button portions 290' 298.

The switch assembly may provide a feedback to the user 30 regarding operation of depression of one or more of the depressible members 290' 298. For example, the switch assembly 100b may provide an audible or tactile click, vibrate, illuminate, etc. Further, separate light emissions portions (e.g., light emitting diodes (LEDs), vibration motors, speakers, etc. may provide auditory, tactile/haptic, and/or optical feedback to the user 30 regarding depression of one or more of the depressible members 290' 298. The feedback may differ, such as a different sound and/or color of light, for each of the depressible members 290' 298.

Figure 11:
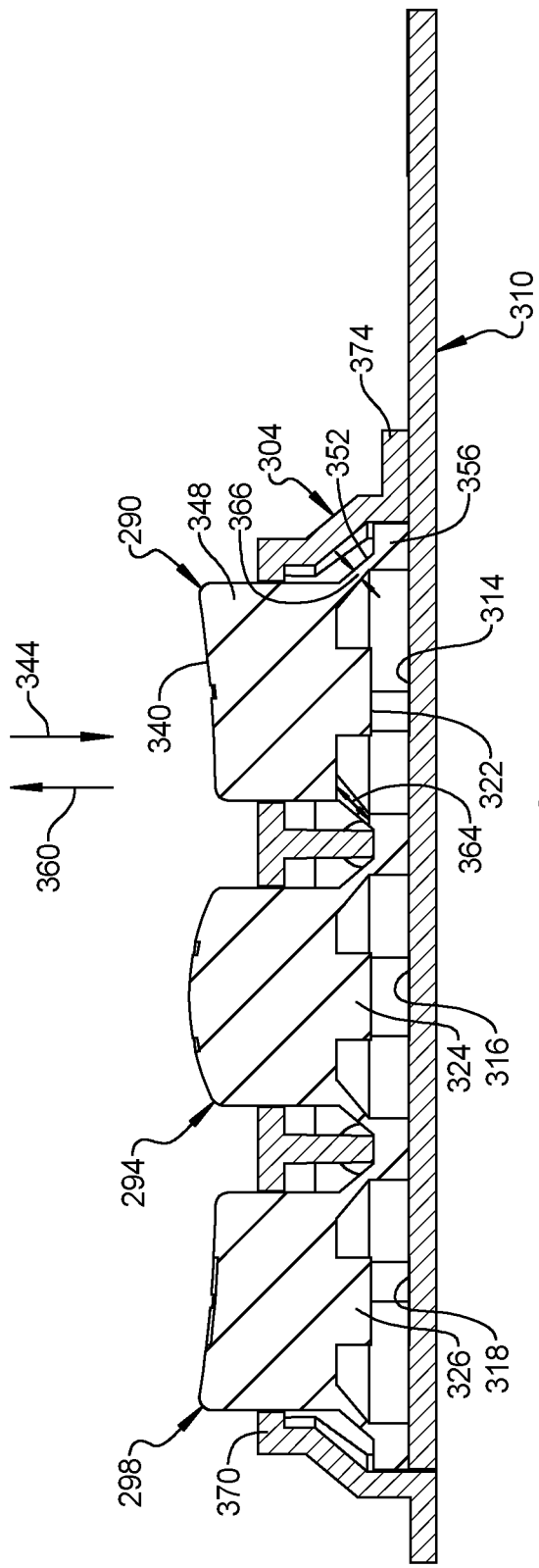
FIG. 11 is a partial cross-sectional view taken along line 11-11 in FIG. 10.

The switch assembly 100b may further include a printed circuit board (PCB) 310. The printed circuit board 310 may include a plurality of traces that form a plurality switch pads 314, 316, and 318. Each of the switch pads 314' 318 may include traces that form circuits that are completed by conductive portions defined or formed by each of the respective individual button portions 290' 298. For example, as illustrated in FIG. 11, each of the individual button portions 290' 298 may include a contact pad or plug 322, 324, 326, respectively. Each of the conductive pads 322' 326 may be formed of selected material, such as a graphite or carbon plug, metal plug, or the like. The contact pads 322' 326 may be positioned to allow for contact with the trace pads 314' 318 to complete a circuit, as discussed herein. The switches or circuits may be completed to provide a signal to the controller 30.

Accordingly the switch assembly 100b may be assembled into the housing 250 such that the PCB 314 is held or positioned relative to various projections, such as switch projections 330, within the housing member, such as the left housing member 250L. The user 30 may grasp the housing 250 and depress or press on one or more of the switch portions 290' 298 to move the conductive plug portion 322' 326 into contact with respective switch or trace pads 314' 318. The housing projections 320 may hold the PCB 310 in place during force applied to the respective button portions 290' 298.

Within particular reference to FIG. 11, each of the button portions may include a similar features as the button 290, which will be discussed in further detail. The button 290 may include an exterior surface 340 that may be contacted and pressed with a selected portion of the user, such as a digit. The exterior surface 340 may be pressed generally in the direction of arrow 344 to move the contact portion 322 into contact with the pad 314 at a selected time. When contact is made, the switch may be sensed to be activated by the system 20.

The button 290 may include a main body portion 348 that defines the exterior surface 340. A biasing portion or surface 352 may be formed to extend between the body portion 348 and a base 356. The base 356 may be positioned on the board 310. The biasing surface or portion 352 may extend around the body portion 248 and bias or hold the body portion 348 at a distance away from the PCB 310. Therefore, the user 30 may overcome the biasing force and press the main body 348 generally in the direction of arrow 344. Once the force of the user 30 is removed, the biasing portion 252 may bias and/or move the main body 348 generally in the direction of arrow 360 such that the conductive pad 322 moves away from the trace pad 314. The biasing portion 252 may include selected dimensions, such as a length or extent dimension 364 of about 0.5 millimeters (mm) to about 3 mm, including about 1.5 mm and a thickness or girth dimension 366 of about 0.2 millimeters (mm) to about 1 mm, including about 0.4 mm. The entire pushbutton member 300, or alternatively, only the biasing portions 252 may be formed of a selected material such as Silicone Rubber with about a 40 Shore A to about a 80 Shore A, including about a 50 Shore A. Thus, the selected dimensions may provide a selected tactile and/or audible feedback to the user 30 regarding operation of each of the depressible members 290' 298, as discussed above. Thus, the feedback, such as haptic feedback, may be integral with the pushbutton member 300.

The cover 304 may be positioned over the button member 300. The cover 304 may include a body or cover surface or region 370 and a board contacting portion 374. Thus the button cover 304 may cover the button portion 300 in the assembly of the instrument 50b.

The switch assembly 100b may include the switch portions that operate similar to that as discussed above including the three buttons 290, 294, and 298. The respective buttons may be used to operate the system 20 in a manner similar to that as discussed above, such as to increase or decrease (including each button having a single operation, such as only increasing or decreasing) a stimulation voltage and/or record a voltage is at the time. Thus, the switch assembly 100b may operate similar to that switch assembly 100a, as discussed above, but it may include the various portions and/or alternative portions as discussed above.

The instrument 50b that includes the probe 158 may be formed such that the probe 158 passes through a distal or probe bore 390 formed or defined through the distal end 258. The probe 158 may be engaged and held within a crimp member 394 similar to that as discussed above. The probe 158 may be formed separately from the housing 250 and passed through the bore or hole 390 and fit into the connector 394. In various embodiments, however, the probe 158 may be over molded during formation of the housing 250L. In various embodiments, in addition and/or alternatively thereto, a sealing member 398 may also be provided around the probe 158 and relative to the housing 250 to assist in sealing and/or holding the probe 158 in a selected position relative to the connector 394 and the housing 250. Accordingly, the instrument 50b may be formed in the plurality pieces into the assembly for use by the user.

Figure 12:
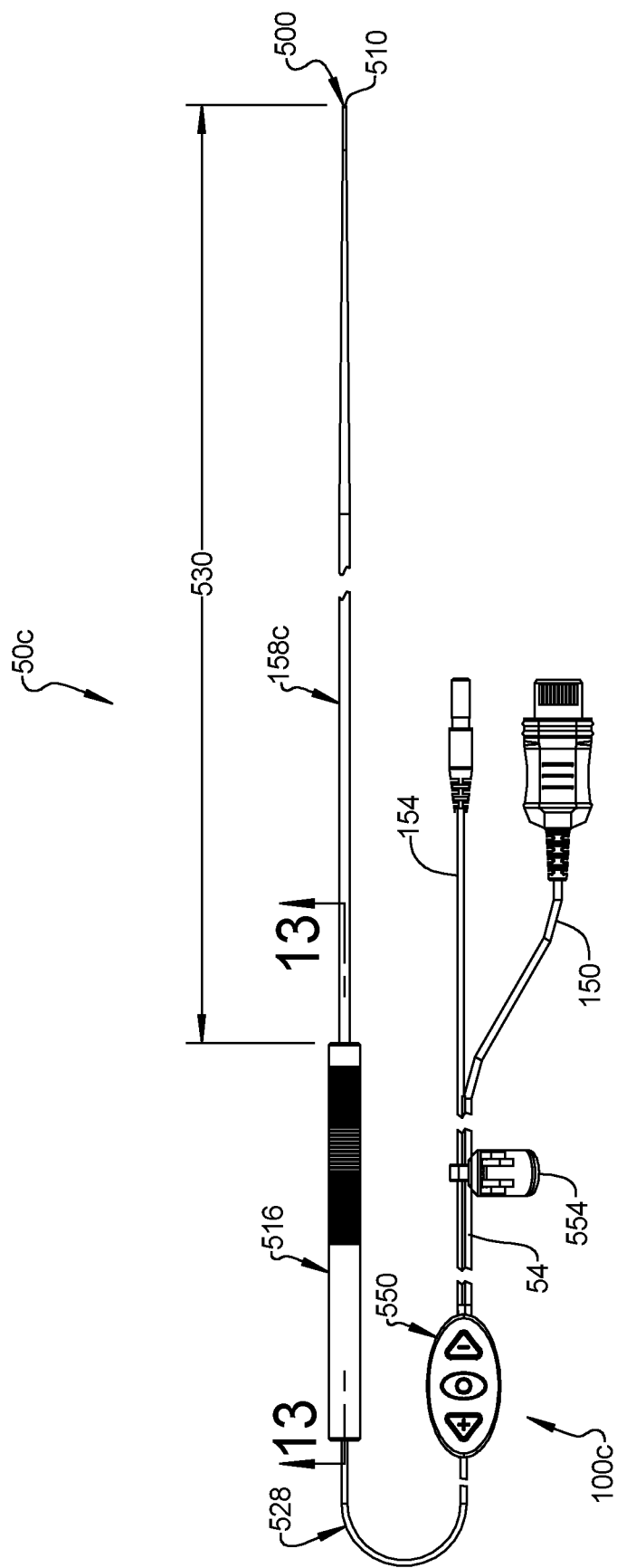
FIG. 12 is a plan view of an instrument handle and connection cable, according to various embodiments.
Figure 13:
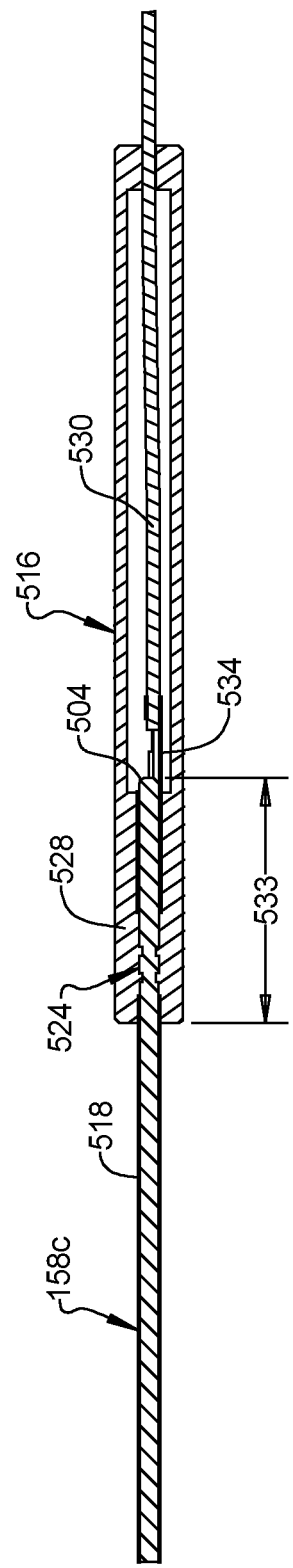
FIG. 13 is a detailed cross-sectional view taken along line 13-13 of FIG. 12.
Figure 14:
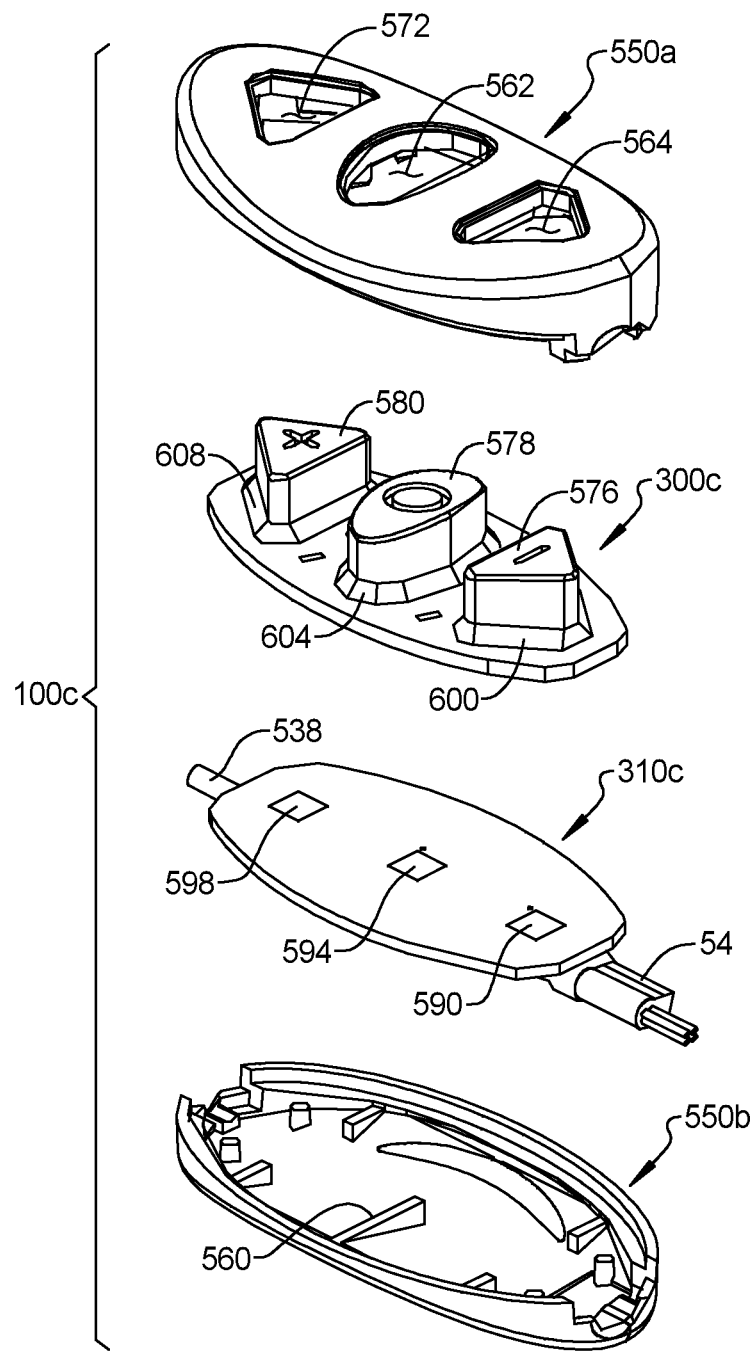
FIG. 14 is an exploded view of the switch assembly 100c of FIG. 11.

With reference to FIG. 12, FIG. 13, and FIG. 14 an instrument assembly 50c is illustrated. The instrument assembly 50c may include a probe 158c that extends between a distal end 500 and a proximal end 504. The proximal end may be held and/or encased within a handle or housing 516 as illustrated in FIG. 13. The housing 516 may be substantially cylindrical and sized and shaped to be grasped and manipulated with less than all of a digits of the hand 30a. For example, the handle 516 may be similar in diameter to a pencil, such as about 1 mm to about 5 centimeters (cm) at a maximum diameter. The distal end 500 may have an exposed tip portion 510 that may contact various selected portions, such as of the subject 34, for providing stimulation thereto. The probe 158c may be covered and/or coated by an insulation material or 518, similar to that discussed above, between the housing 516 and the distal tip 510 to insulate or allow stimulation to be provided only through the distal tip 510. The probe 158c may include the exterior coating 518, as illustrated in FIG. 13, which may be at least partially encapsulated within the housing 516.

The housing 516 may be formed of a substantially insulating material, such as an electrically insulating material. In various embodiments, the housing 516 may be formed of one or more members and/or overmolded onto the probe 158c. For example, the probe 158c may include one or more ridges or projections 524 that may be held or over molded in an overmold portion 528 of the housing 516. In various embodiments, the probe 158c may be held a distance 530 within the handle 516. The distance 530 may be selected for various appropriate purposes and procedures and may include about 10 mm to about 60 centimeters (cm), including about 30 cm to 40 cm, including about 35 cm. Therefore, the probe 158c may be held substantially fixed relative to the housing 516.

Accordingly during use, the user 30 may grasp the housing 516 to manipulate or move the probe 158c. For example, the user 30 may position the distal or stimulating tip 510 relative to the patient 34 for stimulating the selected portion, as discussed above.

Additionally the probe assembly 50c may include leads or connections similar to those discussed above. For example, a crimp connection 534 may connect to the probe 158c within the housing 516. The crimp 534 may be connected to a lead or wire 538 that extends through at least a portion of the housing 516. The lead 538 may be formed of selected cable or wire that extends from a switch assembly 100c. The switch assembly 100c may be similar to the switch assembly 100b, discussed above, save that the switch assembly 100c is a separate unit from the housing 516.

The switch assembly 100c may include a switch housing 550 that encapsulates switching portions, as discussed herein, and is connected with the line or lead 538 to the housing 516 and the connector 534. Extending from the switch assembly 100c may be the conductor or connector 54 that includes or connects with the controller connector 150 and the stimulator connector 154.

Accordingly, the probe assembly 50c may be connected with the stimulation assembly 20, as discussed above, for monitoring or stimulating the subject 34 for selected procedures. The probe assembly 50c may be used for selected applications, for example, when the probe 158c is selected to be a selected length and/or when the housing 516 is selected to be substantially minimal. Further, the probe assembly 50c may include a connector 554 that allows for connection of the connector cabling 54 to a selected material, such as the surgical drape, the dressings of the user 30, or other appropriate positions for connecting the cable 54.

With continued reference to FIG. 12 and further reference to FIG. 14, the switched assembly 100c is illustrated in greater detail. The switch assembly 100c includes the housing 550 which may include a first or top housing 550a and a second or bottom housing portion 550b. The housing 550 including the two portions 550a, 550b, may be assembled to house a button portion 300c that may be positioned adjacent or on a PCB 310c. The button assembly 300c may be similar to the button assembly 300, as discussed above, and the PCB 310c may be similar to the PCB 310, as discussed above. For example, the button portion 300c may provide selected feedback similar to that discussed above. Therefore, the details thereof will not be repeated in detail, but only provided in brevity for the current discussion.

Figure 10:
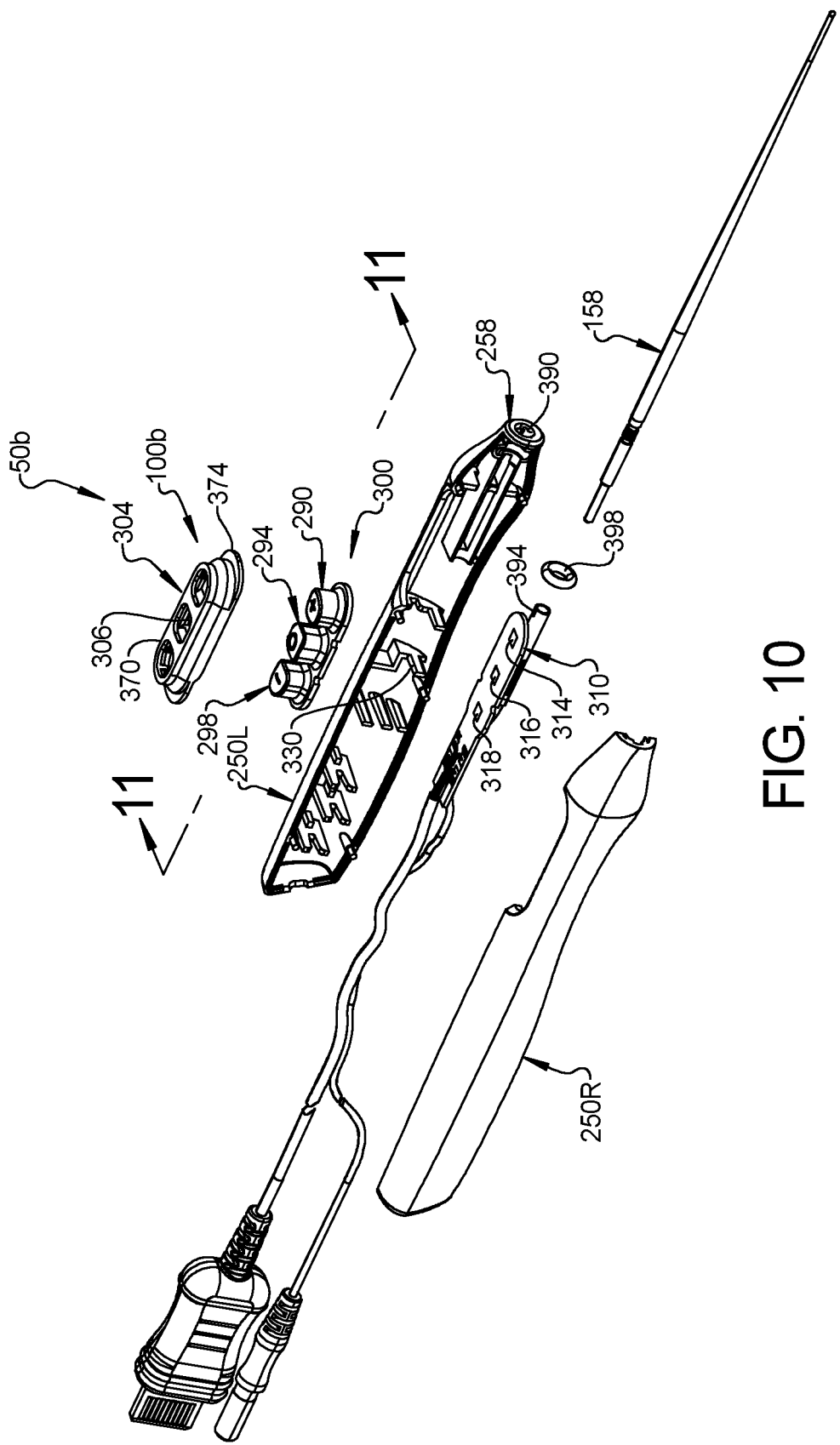
FIG. 10 is an exploded view of the instrument illustrated in FIG. 7.

The button assembly 100c may be similar to the button assembly 100b as discussed above, but be included in the housing 550 separate from another housing, such as the housing 516. Therefore, the handle or housing assembly 516 may not allow for single handed interaction with the button assembly 100c, as illustrated in FIG. 10 of the instrument 50b. Nevertheless, the button assembly 100c may include portions that are substantially similar to the button assembly 100b, as discussed above. Therefore the button assembly 100c will be described with brevity with distinctions provided in detail.

Generally, the housing 550b may include a portions or supports, such as the support 560 that may support the PCB 310c within the housing 550. The top housing portion 550a may be formed to engage the bottom housing 550b to fix the two housing portions 550a, 550b around the button portion 300c and the PCB 310c.

The top housing portion 550a may include passages or openings such as a first passage 564, a second passage 568, and a third passage 572 to allow access to respective button portions. The button portions of the button assembly 300c may include a first button portion 576, a second button portion 578, and a third button portion 580. Each of the button portions 576-580 may extend through the respective openings 564-572 to allow access by the user 30.

The PCB 310c may include pad traces 590, 594, 598 similar to the pad traces 314-318 as discussed above. Each of the button portions 576-580 may include conductive plug portions (not illustrated in FIG. 14) similar to the conductive plug portions 322-326, as discussed above. Similarly, as discussed above, the plug portions may contact the trace portions 590-598 to complete a connection to allow for a signal to be transmitted from the switch assembly 100c. Accordingly the switch assembly 100c, as illustrated in FIG. 14, may include a portion substantially similar to the switch assembly 100d as illustrated in FIG. 11.

The button assembly 300c may interact with the PCB 310c to provide in signals or instructions to the monitor 20 as discussed above. The button assembly 300c may include various portions, such as biasing or flex portion 600, 604, 608, for each of the button portions 576-580. As discussed above the flex portion 600-608 may allow for the button portions 576-580 to be pushed toward the PCB 310c by the user and be biased or moved away from the PCB 310c by the biasing portion 600-608. Therefore the user 30 may press the button portions 576-580 to provide a command or signal to the monitor system 20, as discussed above.

The button assembly 100c, being separate from the handle, such as the handle housing 516, may allow for the button assembly 100c to be positioned for ease of access by the user 30 and/or an alternative user for various purposes. Thus, the button assembly 100c may be usable by one or more users to interact with the monitoring system 20 as discussed above. Nevertheless, the button assembly 100c may also include various portions and/or alternative features, such as those discussed above, to allow for interaction with the monitoring system 20.

As discussed herein, the probe 158 may be provided at various portions. The probe 158, according to various embodiments, may be provided at selected lengths. For example, the probe 158 may extend from a respective housing or handle 50, 516 a length of about be about 80 mm to about 50 cm, including about 5 to about 35 cm. In various embodiments, the probe 158 may have a length from the handle to the distal end of about 80 mm, about 10 cm, and about 95 mm to about 5 cm.

The probe 158, as discussed above, may include the selected distal tip. In various embodiments, the distal tips may be substantially flat and/or include a curved end. In various embodiments, the distal tip may be substantially spherical.

According to various embodiments, the switch portion 100, according to various embodiments, need not be physically connected to the conductor 54 for communicating with the monitoring assembly 20. As discussed above, the conductor 54 allows a signal from the switch portion 100 to be carried to the monitoring assembly 20 and/or a stimulation signal from the monitoring assembly 20 to be delivered through the instrument 50 to the patient 34, such as to the nerve 36. The switch portion 100, however, may include a wireless communication system or portion, such as those generally known in the art, to communicate with the monitoring assembly 20. The switch portion 100 may be operated, as discussed above, however, an instruction from the surgeon 30 may be communicated to the monitoring assembly 20 with a wireless or over the air (OTA) transmission. Also, transmissions from the monitoring assembly 20 regarding operation of the monitoring assembly 20 may be wireless or OTA to the switch portion 100. The conductor 54, or other selected conductor, may be connected to the selected instrument for providing the stimulation to the electrodes. Control, or at least selected control, of the monitoring assembly 20 may be with the switch portion 100 that is wirelessly communicating with the monitoring assembly 20.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Instructions may be executed by a processor and may include may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The apparatuses and methods described in this application may be partially or fully implemented by a special purpose computer created by configuring a general purpose computer to execute one or more particular functions embodied in computer programs. The computer programs include processor-executable instructions that are stored on at least one non-transitory, tangible computer-readable medium. The computer programs may also include or rely on stored data. The computer programs may include a basic input/output system (BIOS) that interacts with hardware of the special purpose computer, device drivers that interact with particular devices of the special purpose computer, one or more operating systems, user applications, background services and applications, etc.

The computer programs may include: (i) assembly code; (ii) object code generated from source code by a compiler; (iii) source code for execution by an interpreter; (iv) source code for compilation and execution by a just-in-time compiler, (v) descriptive text for parsing, such as HTML (hypertext markup language) or XML (extensible markup language), etc. As examples only, source code may be written in C, C++, C#, Objective-C, Haskell, Go, SQL Lisp, Java®, ASP, Perl, Javascript®, HTML5, Ada, ASP (active server pages), Perl, Scala, Erlang, Ruby, Flash®, Visual Basic®, Lua, or Python.

Communications may include wireless communications described in the present disclosure can be conducted in full or partial compliance with IEEE standard 802.11-2012, IEEE standard 802.16-2009, and/or IEEE standard 802.20-2008. In various implementations, IEEE 802.11-2012 may be supplemented by draft IEEE standard 802.11ac, draft IEEE standard 802.11ad, and/or draft IEEE standard 802.11ah.

A processor or module or ̌controller may be replaced with the term ̌circuit. The term module may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A stimulation monitoring system positioned in a non-sterile field separate from a sterile field in which a subject is positioned, the stimulation monitoring system, comprising:
   a conductor physically configured to be connected to a stimulation system;
   a stimulation instrument configured to be positioned within the sterile field near the subject and connected to the stimulation system via the conductor; and
   a switch assembly comprising a plurality of push buttons and a plurality of switches;
   wherein the switch assembly is included with the stimulation instrument;
   wherein each push button of the plurality of push buttons is configured to engage one switch of the plurality of switches;
   wherein each switch is configured to provide a signal to the stimulation system for operation of the stimulation system;
   wherein the stimulation instrument is operable to deliver a generated stimulation from the stimulation system;
   wherein each switch of the plurality of switches is operable to provide a feedback to a user;
   wherein the feedback includes at least one of a haptic feedback, an audible click, an optical feedback, or combinations therefore;
   wherein the stimulation instrument further comprises:
      a housing;
      a stimulation probe extending from the housing;
      wherein the housing houses the switch assembly; and
   wherein an exterior wall of the housing includes a waist region having a first circumference and an enlarged distal region having a second circumference, the second circumference larger than the first circumference to provide an indication of an orientation.

2. The stimulation monitoring system of claim 1, wherein each push button of the plurality of push buttons comprises:
   an external surface configured to extend from the housing to be directly engaged by a digit;
   an engaging portion configured to selectively engage one switch of the plurality of switches; and
   a rocker portion configured to engage a coupling of the housing to allow the push button to move relative to the housing.

3. The stimulation monitoring system of claim 1, further comprising:
   the stimulation system configured to generate a stimulation signal;

wherein the conductor includes a first portion connected to the plurality of switches and a second portion connected to the stimulation probe;
wherein the stimulation signal is operable to transmitted from the stimulation system directly to the stimulation probe.

4. The stimulation monitoring system of claim 3, further comprising:
a printed circuit board;
wherein the plurality of switches are connected to the printed circuit board;
wherein the first portion of the conductor is connected to the printed circuit board.

5. The stimulation monitoring system of claim 4, wherein the switches are sealed to the printed circuit board.

6. The stimulation monitoring system of claim 1, further comprising:
a printed circuit board fixed within the housing;
wherein the plurality of switches are connected to the printed circuit board;
wherein the push buttons are moveably mounted within the housing to allow movement of the push buttons relative to the plurality of switches to selectively operate the plurality of switches.

7. A stimulation monitoring system positioned in a non-sterile field separate from a sterile field in which a subject is positioned, the stimulation monitoring system, comprising:
a conductor physically connected to a stimulation system; and
a stimulation instrument configured to be positioned within the sterile field near the subject and connected to a stimulation system via the conductor;
a switch assembly comprising a plurality of push buttons each having an exterior surface engagable by a user and an opposed internal conductive portion and a printed circuit board including a plurality of conductive trace pads, wherein the switch assembly is included with the stimulation instrument;
wherein the exterior surface of each push button of the plurality of push buttons is configured to be engaged by the user so that each opposed internal conductive portion engage one conductive trace pad of the plurality of conductive trace pads;
wherein each conductive trace pads is configured to provide a signal to the stimulation system for operation of the stimulation system.

8. The stimulation monitoring system of claim 7, wherein the stimulation instrument further comprises:
a housing; and
a stimulation probe extending from the housing;
wherein the housing houses the switch assembly;
wherein each push button of the plurality of push buttons is operable to provide a switch feedback to a user.

9. The stimulation monitoring system of claim 8, wherein the housing includes an inner wall configured to fix the stimulation probe relative to the housing.

10. The stimulation monitoring system of claim 8, wherein the exterior wall includes a narrow waist region and an enlarged distal region to provide an indication of an orientation to the user.

11. The stimulation monitoring system of claim 8, wherein the housing includes an inner wall configured to fix the printed circuit board relative to the housing;
wherein each push button of the plurality of push buttons includes a biasing portion to bias each push button of the plurality of push buttons away from the printed circuit board;
wherein the plurality of push buttons each are formed together as a single push button member having a base fixed relative to the printed circuit board.

12. The stimulation monitoring system of claim 11, further comprising:
a pushbutton cover member having a plurality of passages to allow access to each push button of the plurality of push buttons.

13. The stimulation monitoring system of claim 7, further comprising:
the stimulation system configured to generate a stimulation signal;
wherein the stimulation instrument further comprises:
a probe housing; and
a stimulation probe extending from the probe housing; and
a switch assembly housing configured to house the switch assembly;
wherein the probe housing has an exterior wall configured to be grasped by a user.

14. The stimulation monitoring system of claim 13, wherein the probe housing is substantially cylindrical and includes a unitary distal end that secures the stimulation probe to the probe housing.

15. The stimulation monitoring system of claim 13, wherein the probe housing is spaced apart and separate from the switch assembly housing.

16. A method of controlling a stimulation monitoring system to monitor a stimulation provided to a subject through a stimulation instrument from the stimulation monitoring system having a stimulation system, the method comprising:
providing the stimulation instrument with a switch assembly to be positioned within a sterile field;
providing a physical connection configured to physically connect the stimulation instrument within the sterile field and the stimulation monitoring system having the stimulation system to be positioned in a non-sterile field away from the sterile field, such that the switch assembly is operable to be connected to the stimulation monitoring system having the stimulation system to selectively control the stimulation monitoring system;
providing a plurality of switches within the switch assembly to selectively operate the stimulation monitoring system having the stimulation system from within the sterile field;
providing a housing that houses the switch assembly and fixes a stimulation probe to the housing; and
providing an indication of an orientation of the stimulation instrument by providing a waist in the housing having a first circumference and an enlarged end having a second circumference, the second circumference larger than the first circumference.

17. The method of claim 16, wherein the plurality of switches allow operation of the stimulation monitoring system having the stimulation system while performing a procedure with the stimulation instrument on the subject.

18. The method of claim 16, further comprising:
configuring the switches to be manipulated to generate a signal to be transmitted to the stimulation monitoring system having the stimulation system for operation of the stimulation monitoring system having the stimulation system.

19. The method of claim 16, further comprising:
providing the plurality of switches within the housing; and providing a feedback to a user upon operation of each switch of the plurality of switches, wherein the feedback includes at least one of an audible click, haptic feed, optical feedback, or a combination thereof.

20. The method of claim 16, wherein fixing the probe to the housing includes overmolding the housing onto the probe.

* * * * *